(12) United States Patent
Saetveit et al.

(10) Patent No.: US 10,060,541 B1
(45) Date of Patent: *Aug. 28, 2018

(54) VALVE ASSEMBLY WITH BOTTOM BYPASS PORTS

(71) Applicant: Elemental Scientific, Inc., Omaha, NE (US)

(72) Inventors: Nathan Saetveit, Omaha, NE (US); Daniel R. Wiederin, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/400,654

(22) Filed: Jan. 6, 2017

Related U.S. Application Data

(63) Continuation of application No. 14/612,494, filed on Feb. 3, 2015, now Pat. No. 9,541,207.

(60) Provisional application No. 61/935,024, filed on Feb. 3, 2014.

(51) Int. Cl.
| | | |
|---|---|---|
| *F16K 11/085* | (2006.01) | |
| *F16K 11/10* | (2006.01) | |
| *G01N 30/20* | (2006.01) | |
| *F16K 11/074* | (2006.01) | |

(52) U.S. Cl.
CPC ...... *F16K 11/0743* (2013.01); *F16K 11/0853* (2013.01); *F16K 11/10* (2013.01); *G01N 30/20* (2013.01); *G01N 2030/202* (2013.01)

(58) Field of Classification Search
CPC .............. G01N 2030/202; G01N 30/20; F16K 11/0853; F16K 11/10
See application file for complete search history.

(56) References Cited

U.S. PATENT DOCUMENTS

| | | |
|---|---|---|
| 3,508,582 A | 4/1970 | Aulisa |
| 3,868,970 A | 3/1975 | Ayers et al. |
| 4,552,178 A | 11/1985 | Olsson |
| 4,625,569 A | 12/1986 | Toei et al. |
| 5,105,851 A | 4/1992 | Fogelman |
| 5,803,117 A | 9/1998 | Olsen et al. |
| 6,012,487 A | 1/2000 | Hauck |
| 6,502,448 B1 | 1/2003 | Rapkin |
| 6,672,336 B2 | 1/2004 | Nichols |
| 8,047,060 B2 | 11/2011 | Dourdeville et al. |
| 8,322,197 B2 | 12/2012 | Koster et al. |
| 8,944,102 B1 | 2/2015 | Wiederin et al. |
| 9,146,182 B1 | 9/2015 | Wiederin et al. |
| 9,541,207 B1 * | 1/2017 | Saetveit .............. F16K 11/0743 |
| 2013/0276520 A1 | 10/2013 | Moeller |
| 2014/0007600 A1 | 1/2014 | Johnson et al. |
| 2015/0047730 A1 | 2/2015 | Dourdeville et al. |

* cited by examiner

*Primary Examiner* — Craig Schneider
*Assistant Examiner* — Kevin Barss
(74) *Attorney, Agent, or Firm* — Kevin E. West; Advent, LLP

(57) ABSTRACT

A rotor, a valve assembly, and a method for using the rotor and valve assembly are described that provide a reversed flow path. In an implementation, a rotor that employs example techniques in accordance with the present disclosure includes a plurality of channels formed in a surface of the rotor, the surface configured to be adjacent to and interface with a stator having a plurality of ports, where at least one channel fluidically connects at least three of the plurality of ports.

17 Claims, 13 Drawing Sheets

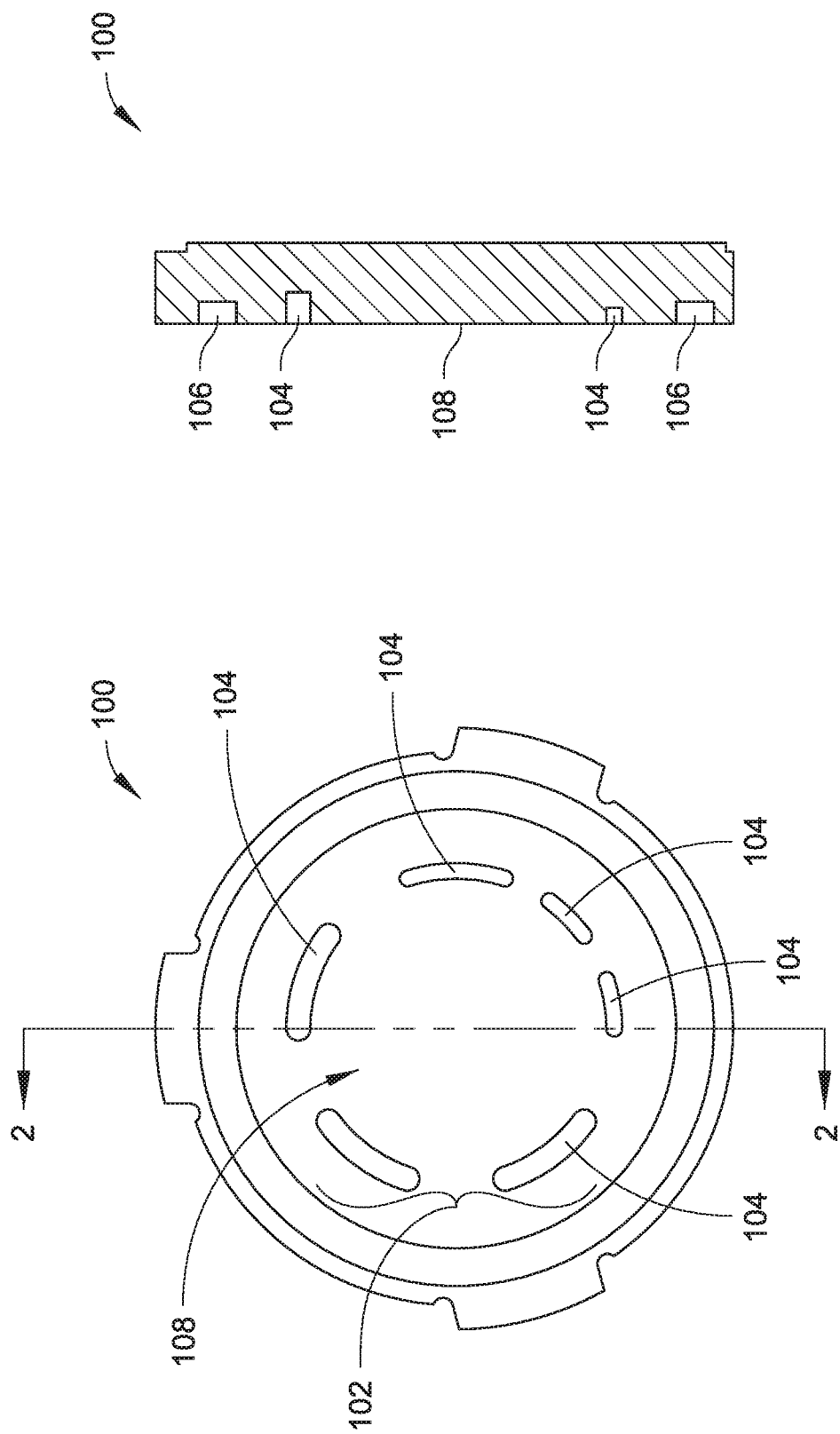

VALVE ASSEMBLY WITH BOTTOM BYPASS PORTS

The present application is a continuation under 35 U.S.C. § 120 of U.S. patent application Ser. No. 14/612,494, filed Feb. 3, 2015, and titled "VALVE ASSEMBLY WITH BOTTOM BYPASS PORTS," which itself claims the benefit of 35 U.S.C. § 119(e) of U.S. Provisional Application Ser. No. 61/935,024, filed Feb. 3, 2014, and titled "VALVE ASSEMBLY WITH BOTTOM BYPASS PORTS." U.S. patent application Ser. No. 14/612,494 and U.S. Provisional Application Ser. No. 61/935,024 are herein incorporated by reference in their entireties.

BACKGROUND

Inductively Coupled Plasma (ICP) spectrometry is an analysis technique commonly used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample.

Sample introduction systems may be employed to introduce the liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. The aerosol is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

A rotor, a valve assembly, and a method for using the rotor and valve assembly are described that provide a reversed flow path. In an implementation, a rotor that employs example techniques in accordance with the present disclosure includes a plurality of channels formed in a surface of the rotor, the surface configured to be adjacent to and interface with a stator having a plurality of ports, the plurality of ports including a first port configured to connect to a column, a second port configured to connect to at least one of an eluent or a diluent, a third port, a fourth port configured to connect to the column, a fifth port configured to connect to a buffer, and a sixth port configured to connect to waste, the plurality of channels fluidically connecting at least one of the first port, the second port, the third port, the fourth port, the fifth port, or the sixth port with at least one other of the first port, the second port, the third port, the fourth port, the fifth port, or the sixth port, and at least one channel that fluidically connects at least three of the plurality of ports.

In an implementation, a valve assembly that employs example techniques in accordance with the present disclosure includes a first valve member; and a second valve member comprising a plurality of ports including a first port configured to connect to a column, a second port configured to connect to at least one of an eluent or a diluent, a third port, a fourth port configured to connect to the column, a fifth port configured to connect to a buffer, and a sixth port configured to connect to waste; the first valve member comprising a plurality of channels configured to interface with the second valve member so that the second port is connected to the third port and the fourth port is connected to the fifth port in a first flow configuration, and the first port is connected to the second port and the fourth port is connected to the fifth port and the sixth port in a second flow configuration.

In an implementation, a process that employs example techniques in accordance with the present disclosure includes implementing a first flow configuration using a valve assembly including a first valve member; and a second valve member comprising a plurality of ports including a first port configured to connect to a column, a second port configured to connect to at least one of an eluent or a diluent, a third port, a fourth port configured to connect to the column, a fifth port configured to connect to a buffer, and a sixth port configured to connect to waste; the first valve member comprising a plurality of channels configured to interface with the second valve member so that the second port is connected to the third port and the fourth port is connected to the fifth port in the first flow configuration, and the first port is connected to the second port and the fourth port is connected to the fifth port and the sixth port in a second flow configuration; and reversing the first flow configuration to implement the second flow configuration by rotating the second valve member such that a sample flow is injected into a nebulizer.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

FIG. 1 is a front view illustrating a rotor for a multiport flow valve assembly in accordance with an example embodiment of the present disclosure.

FIG. 2 is a cross-sectional side view of the rotor illustrated in FIG. 1.

DETAILED DESCRIPTION

Overview

Figure 3:
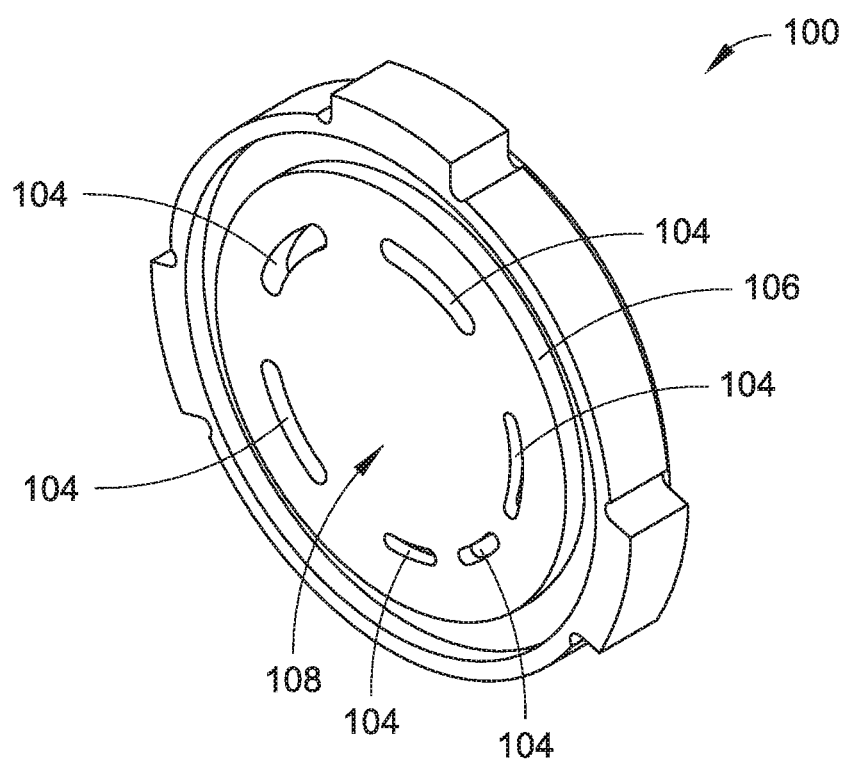
FIG. 3 is an isometric view of the rotor illustrated in FIG. 1.
Figure 4:
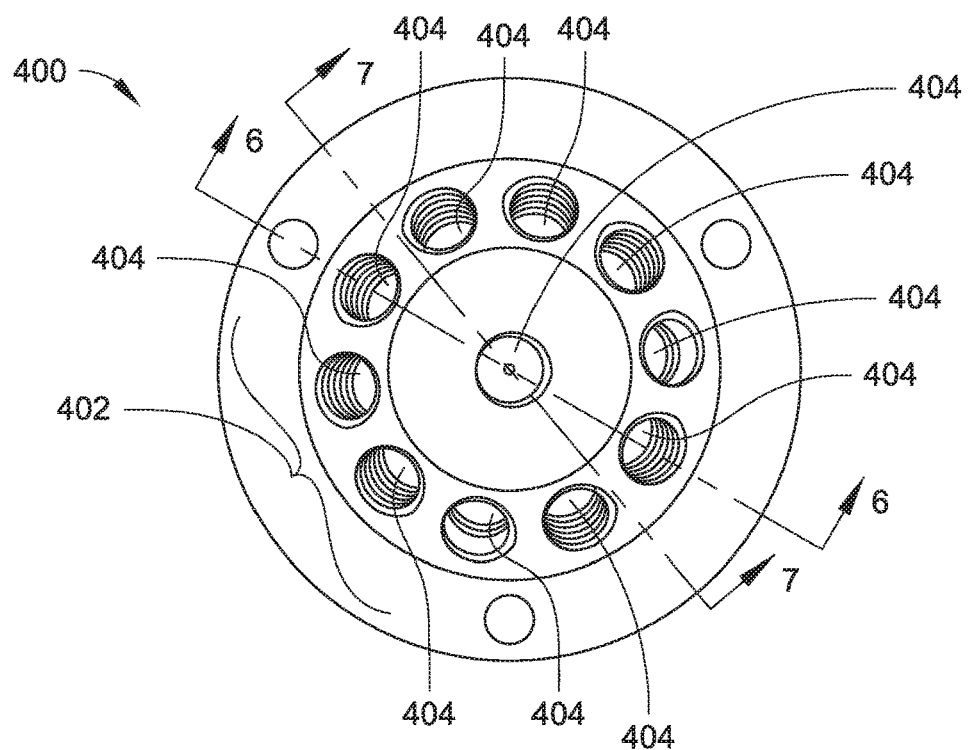
FIG. 4 is a front view illustrating a stator for a multiport flow valve assembly in accordance with an example embodiment of the present disclosure.
Figure 5:
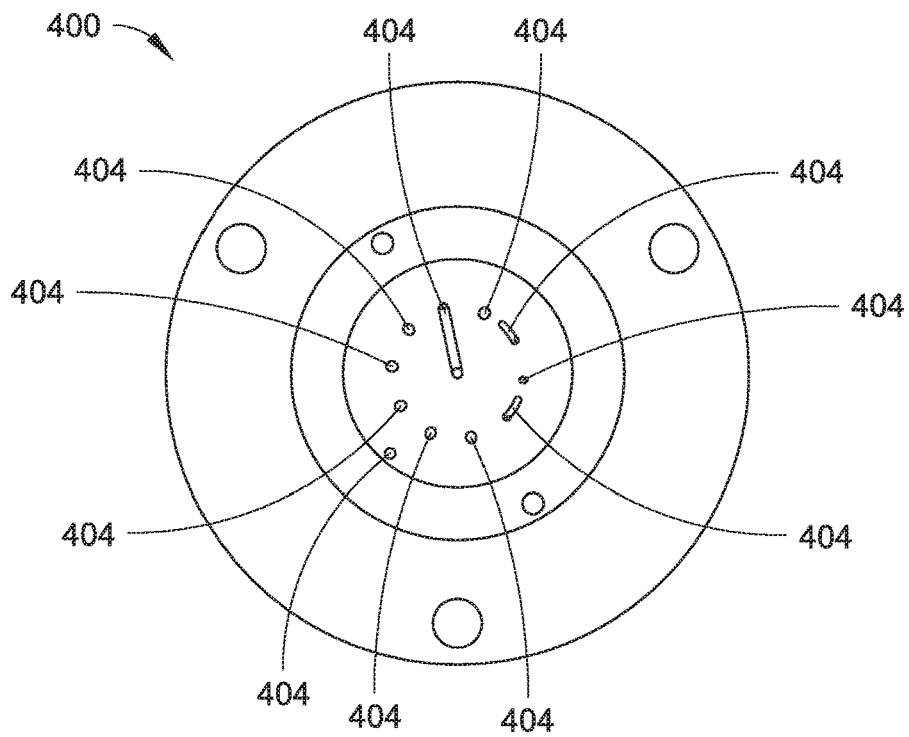
FIG. 5 is a back view of the stator illustrated in FIG. 4.
Figure 6:
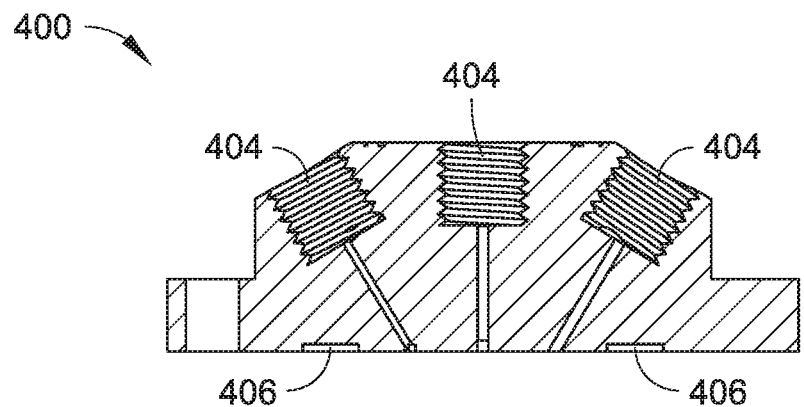
FIG. 6 is a cross-sectional side view of the stator illustrated in FIG. 4.
Figure 7:
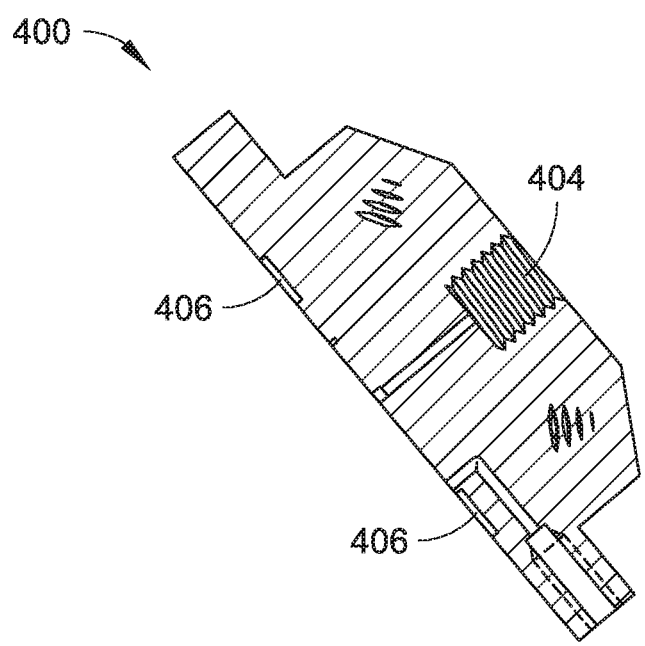
FIG. 7 is another cross-sectional side view of the stator illustrated in FIG. 4.

Multiport valves are often used to transport sample materials to laboratory equipment for analysis. For example, multiport valves can be used to introduce liquid samples into ICP spectrometry instrumentation for analysis. Multiport valves can also be used to load samples on columns for liquid and/or gas chromatography. Some valves used in these applications include six-port (6-port), two-position (2-position) rotary valves. Generally, two ports of a rotary valve are connected to an external (sample) loop, one port is connected to a sample source, another port is connected to a carrier source, a further port is connected to a vent (waste), and another port is connected to a nebulizer/column. When the valve is in a first orientation, sample from the sample source flows through the sample loop, while carrier from the carrier source flows directly to a nebulizer/column. When the valve is rotated to a second orientation, the carrier source is connected to the sample loop for injecting the sample contained in the sample loop into the nebulizer or onto the column. However, these valves are somewhat limited in the configurations available to direct fluid paths because it can be difficult to reverse a flow path.

Accordingly, a rotor, a valve assembly, and a method for using the rotor and valve assembly are described that provide a reversed flow path. In an implementation, a rotor that employs example techniques in accordance with the present disclosure includes a plurality of channels formed in a surface of the rotor, the surface configured to be adjacent to and interface with a stator having a plurality of ports, the plurality of ports including a first port configured to connect to a column, a second port configured to connect to at least one of an eluent or a diluent, a third port, a fourth port configured to connect to the column, a fifth port configured to connect to a buffer, and a sixth port configured to connect to waste, the plurality of channels fluidically connecting at least one of the first port, the second port, the third port, the fourth port, the fifth port, or the sixth port with at least one other of the first port, the second port, the third port, the fourth port, the fifth port, or the sixth port, and at least one channel that fluidically connects at least three of the plurality of ports.

In an implementation, a valve assembly that employs example techniques in accordance with the present disclosure includes a first valve member; and a second valve member comprising a plurality of ports including a first port configured to connect to a column, a second port configured to connect to at least one of an eluent or a diluent, a third port, a fourth port configured to connect to the column, a fifth port configured to connect to a buffer, and a sixth port configured to connect to waste; the first valve member comprising a plurality of channels configured to interface with the second valve member so that the second port is connected to the third port and the fourth port is connected to the fifth port in a first flow configuration, and the first port is connected to the second port and the fourth port is connected to the fifth port and the sixth port in a second flow configuration.

In an implementation, a process that employs example techniques in accordance with the present disclosure includes implementing a first flow configuration using a valve assembly including a first valve member; and a second valve member comprising a plurality of ports including a first port configured to connect to a column, a second port configured to connect to at least one of an eluent or a diluent, a third port, a fourth port configured to connect to the column, a fifth port configured to connect to a buffer, and a sixth port configured to connect to waste; the first valve member comprising a plurality of channels configured to interface with the second valve member so that the second port is connected to the third port and the fourth port is connected to the fifth port in the first flow configuration, and the first port is connected to the second port and the fourth port is connected to the fifth port and the sixth port in a second flow configuration; and reversing the first flow configuration to implement the second flow configuration by rotating the second valve member such that a sample flow is injected into a nebulizer.

Example Implementations

As shown in FIGS. 1 through 15, a valve assembly 800 includes a first valve member (e.g., a rotor 100) and a second valve member (e.g., a stator 400). FIGS. 1 through 8 illustrate an example stator 400 and an example rotor 100 for a valve assembly 800. The valve assembly 800 includes a first valve member and a second valve member coupled adjacent to the first valve member. As shown, the valve assembly 800 can be configured as a rotary valve assembly having a first valve member comprising a rotor 100 and a second valve member comprising a stator 400 coupled adjacent to the rotor 100 so that the rotor 100 can rotate with respect to the stator 400. The valve assembly 800 is configured to furnish a high degree of mixing between two or more fluids (e.g., a sample fluid 908 and a diluent 906 and/or an internal standard) supplied to instrumentation, such as ICP spectrometry instrumentation, and so forth. In implementations, the valve assembly 800 provides a high degree of mixing at high dilution factors (DF), and can provide more reproducible stabilization times (e.g., for ICP spectrometry) at various dilution factors. It should be noted that while the accompanying figures show the rotor 100 and the stator 400 of the valve assembly 800, the valve assembly 800 may also include additional components, such as components for holding the rotor 100 adjacent to the stator 400, and so forth. For example, the valve assembly 800 may further include a drive configured to rotate the rotor 100 and/or the stator 400, and a housing configured to support the stator 400 and/or the rotor 100 adjacent to the stator 400.

Figure 10:
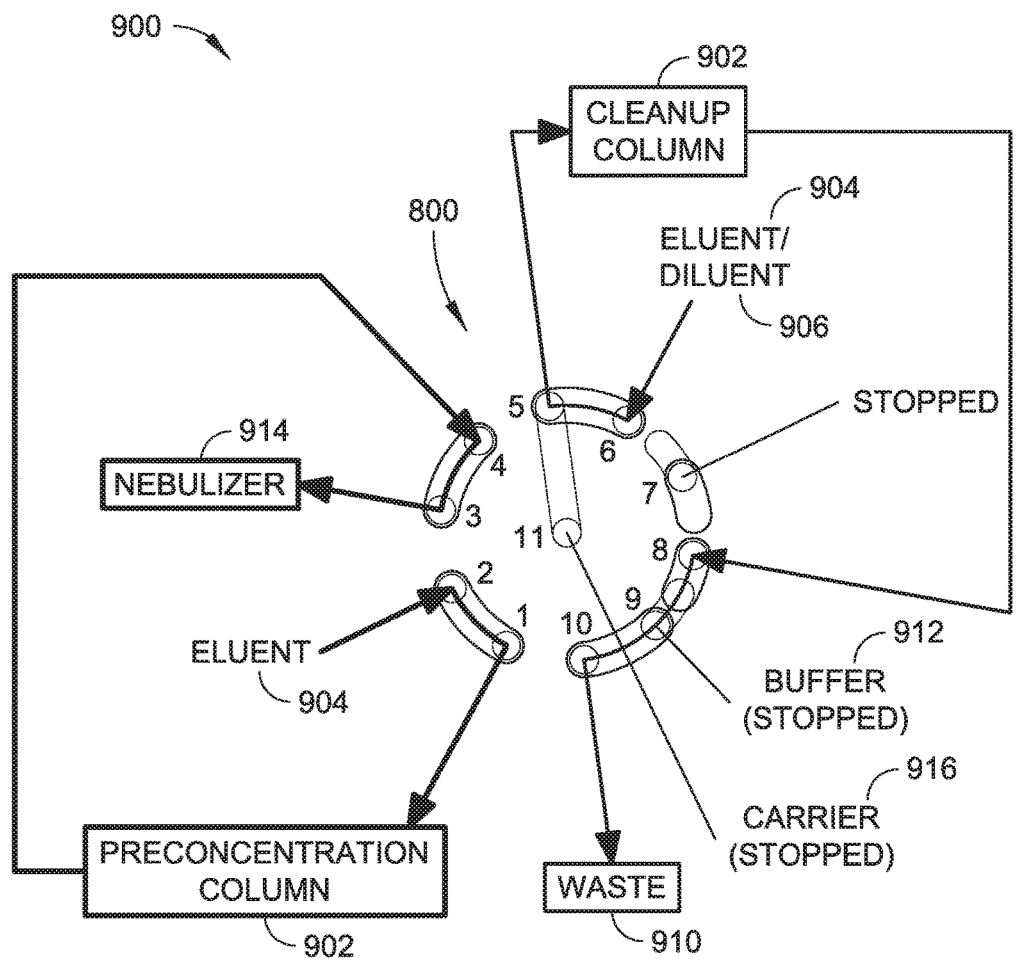
FIG. 10 is a diagrammatic illustration of the system shown in FIG. 9, where the multiport flow valve assembly is arranged in an inject configuration in accordance with an example embodiment of the present disclosure.

As shown in FIGS. 1 through 3, the valve assembly 800 includes a first valve member. In implementations, the first valve member can include a rotor 100. In one example, the rotor 100 can include at least one channel 104 configured to connect a first port on a stator 400 to a second port on the stator 400 in a first (loading) configuration for charging a sample loop or column 902 with a sample fluid 908, and to connect the sample loop or column 902 to a nebulizer 914 in a second (injection) orientation for supplying the sample fluid 908 from the sample loop or column 902 to the nebulizer 914. In some examples, a channel 104 can fluidically connect more than one port of a stator 400 (e.g., one example shown in FIG. 10 illustrates an eighth port 8 connected to a ninth port 9 and a tenth port 10). For example, the rotor 100 includes a first channel 104 configured to connect the second port 2 to the third port 3 in the first orientation, and to connect the first port 1 to the second port 2 in the second orientation. The rotor 100 can also include a second channel 140 configured to connect the fourth port 4 to the fifth port 5 in the first orientation, and to connect the third port 3 to the fourth port 4 in the second orientation. The rotor 100 can further include a third channel 3 configured to connect the sixth port 6 to the first port 1 in the first orientation, and to connect the fifth port 5 to the sixth port 6 in the second orientation for supplying the sample fluid 908 from the sample loop or column 902 to the nebulizer 914. FIGS. 1-3, illustrate six different channels 104 where the channels include different configurations. It is contemplated that other configurations including numbers of ports and the configuration of ports can be utilized.

As shown in FIGS. 4 through 8, the valve assembly 800 includes a second valve member, which can further include a stator 400. The stator 400 can include ports configured to connect to an external loop (e.g., a sample loop or a column 902), an output (e.g., a nebulizer 914), and/or a vent/waste 910. In one embodiment, the stator 400 is configured to receive a first fluid (e.g., a carrier fluid 916), a second fluid (e.g., a sample fluid 908), a third fluid (e.g., a diluent 906/internal standard), and/or a fourth fluid (e.g., an internal standard/diluent 906). It is contemplated that other fluids and/or types of fluids may be utilized. The stator 400 can include a first port 1 configured to connect to the sample loop or column 902, a second port 2 configured to receive the carrier 916, a third port 3 configured to receive the diluent 906/internal standard, a fourth port 4 configured to connect to the sample loop or column 902, a fifth port 5 configured to receive the sample fluid 908, a sixth port 6 configured to connect to waste 910, and/or a seventh port 7 configured to connect to the nebulizer 914. In some implementations, the stator 400 may also include an eighth port 8 configured to connect to the nebulizer 914. The eighth port 8 may be positioned in the side of the stator 400 to furnish online dilution of, for example, the sample fluid 908. For instance, a source of internal standard/diluent 906 can be connected to the eighth port 8, and the internal standard/diluent 906 can be supplied while the sample fluid 908 and/or the diluent 906/internal standard is pumped to the nebulizer 914. The eighth port 8 may also be used to provide a rinse for rinsing the connection to the nebulizer 914. In implementations, the stator 400 may also include a drain port, which may be connected to a channel 104 in the rotor 100. In implementations, fluid flow to the ports of the stator 400 can be controlled using an instrument such as a valve controller (not shown). In the embodiment shown in FIGS. 4-5 and 8, eleven ports are illustrated. However, it is contemplated that other numbers or types of ports can be utilized.

Figure 8:
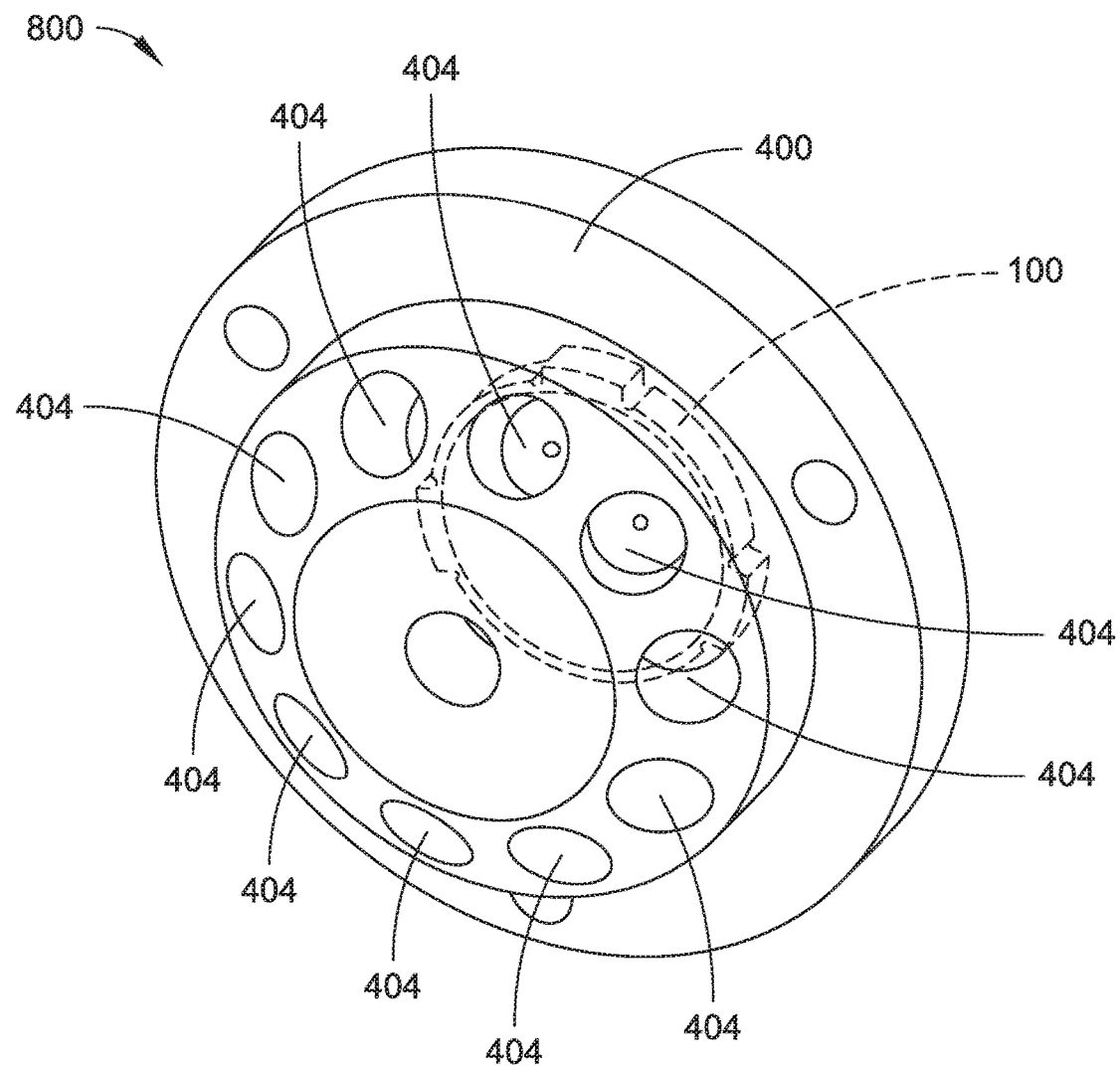
FIG. 8 is an isometric view illustrating a multiport flow valve assembly including a rotor, such as the rotor illustrated in FIG. 1, and a stator, such as the stator illustrated in FIG. 4, in accordance with an example embodiment of the present disclosure.

In a specific implementation shown in FIG. 8, the valve assembly 800 includes a stator 400 comprising a first port 1 configured to connect to a column 902, a second port 2 configured to connect to at least one of an eluent 904 or a diluent 906, a third port 3, a fourth port 4 configured to connect to the column 902, a fifth port 5 configured to connect to a buffer 912, and a sixth port 6 configured to connect to waste 910. The valve assembly 800 also includes a rotor 100 comprising a plurality of channels 104 configured to interface with the stator 400 so that the second port 2 is connected to the third port 3 and the fourth port 4 is connected to the fifth port 5 in a first configuration (e.g., a load configuration), and the first port 1 is connected to the second port 2 and the fourth port 4 is connected to the fifth port 5 and the sixth port 6 in a second configuration (e.g., an inject configuration). For example, the third port 3 of the stator 400 includes a first channel 104 configured to connect the second port 2 to the third port 3 in the load configuration, and the fifth port 5 of the stator 400 comprises a second channel 104 configured to connect the fourth port 4 to the fifth port 5 in the inject configuration.

It should be noted that while the terms "stator" and "rotor" are used herein to describe the first and second valve members, these terms are provided by way of example only (e.g., to illustrate how these components interface (e.g., rotate) with respect to one another), and are not meant to limit how the valve members can be actuated with respect to an external reference (e.g., valve mounting hardware, or the like). Thus, in one particular example, a component described as a "stator" may remain substantially stationary (e.g., with respect to an external reference, such as valve mounting hardware), and a component described as a "rotor" may rotate with respect to the stator. However, in another particular example, a component described as a "stator" may rotate with respect to a rotor, and a component described as a "rotor" may remain substantially stationary (e.g., with respect to valve mounting hardware). Further, in some implementations, both a component described as a "stator" and a component described as a "rotor" may rotate with respect to an external reference.

Figure 9:
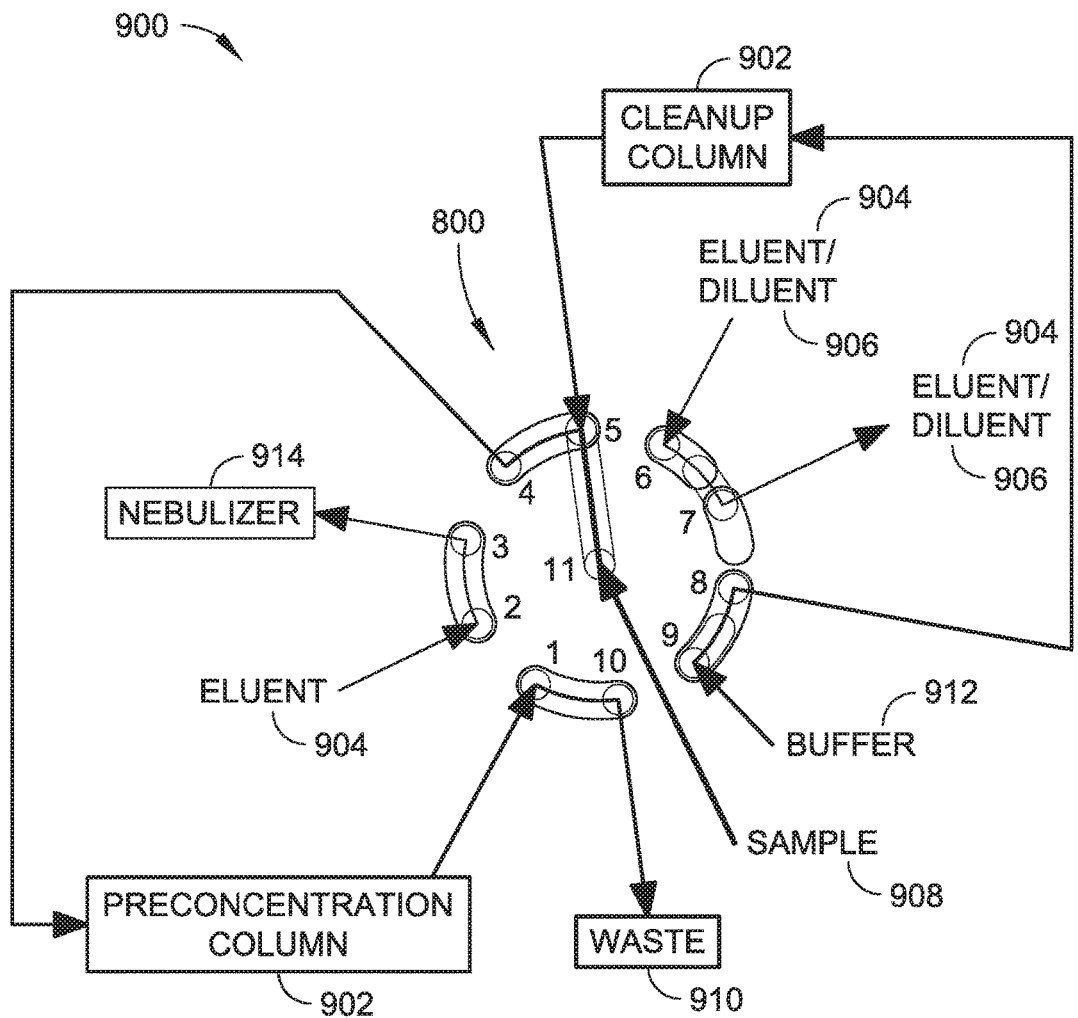
FIG. 9 is a diagrammatic illustration of a system including a multiport flow valve assembly, such as the multiport flow valve assembly illustrated in FIG. 8, where the multiport flow valve assembly is arranged in a load configuration in accordance with an example embodiment of the present disclosure.

An exemplary loading configuration is shown in FIG. 9. In this specific configuration, a sample 908 is loaded into a valve assembly 800, which includes a rotor 100 having multiple channels 104 configured to fluidically connect eleven ports and includes a stator 400 having eleven ports. In this loading configuration, a sample 908 is first loaded into a port 11 and further directed to ports 5 and port 4 via a channel 104 and into a column 902 that is connected to port 4. Excess sample is pumped through column 902 to port 1, which is fluidically connected to port 10 and waste 910. Simultaneously, a buffer 912 is pumped into port 9, which is fluidically connected to port 8, and thorough a cleanup column 902 into port 5 where it is mixed with sample 908. Additionally, a diluent 906, an eluent 904, and/or a carrier can be pumped in and out of the other ports (e.g., port 2, port 3, port 6, port 7, etc.).

An exemplary injection configuration is shown in FIG. 10. In this specific configuration, the rotor 100 is rotated from the rotor position for the configuration (e.g., a loading configuration) shown in FIG. 9. Here, the sample 908 previously loaded into preconcentration column 902 from port 4 is now pumped (along with an eluent pumped into port 2, which is fluidically connected to port 1) from the preconcentration column 902 to port 4 and port 3 (via a channel 104 in the rotor 100) to a nebulizer 914. Because the rotor 100 is rotated to an injection configuration, the flow through ports 5-10 (e.g., of an eluent 904/diluent 906/carrier 916) is either stopped or reversed. In the example shown in FIG. 10, eluent 904/diluent 906 can be pumped to port 6 and out port 5 (fluidically connected via a channel 104), through cleanup column 902 to port 8 and out port 10 to waste 910. Here, port 7, port 9, and port 11 are stopped due to the channel 104 configuration in rotor 100. The channel 104 in rotor 100 that fluidically connects port 8 with port 10 is larger (e.g., longer) than some of the other channels in rotor 100 thereby allowing for ports that are not adjacent to each other (e.g., port 8 and port 10) to be fluidically connected and enable a reverse fluid flow through the cleanup column 902.

Figure 11:
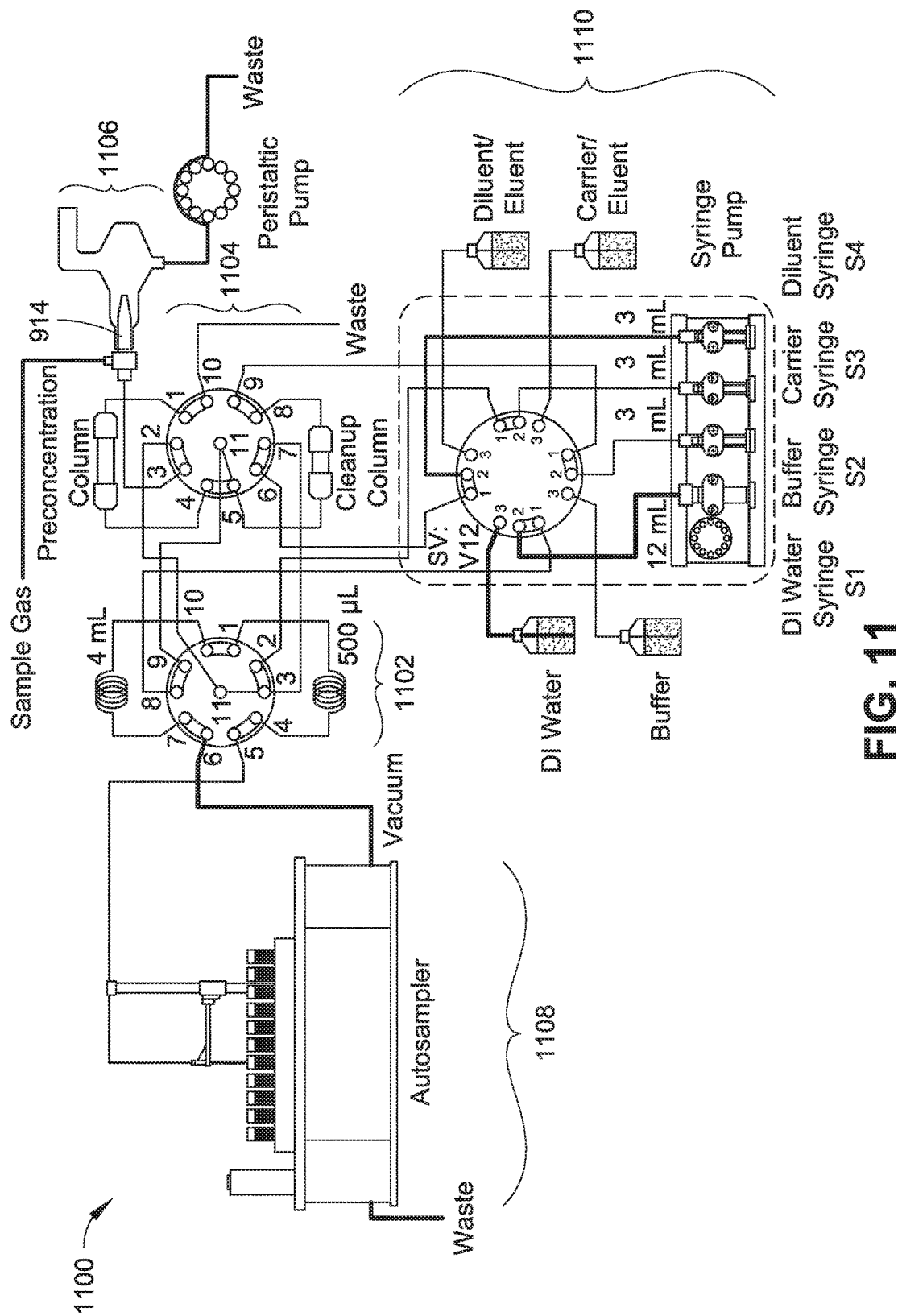
FIG. 11 is a diagrammatic illustration of a system including a first multiport flow valve assembly, such as the multiport flow valve assembly illustrated in FIG. 8, and a second multiport flow valve assembly in accordance with an example embodiment of the present disclosure.

In some implementations, a system 1100 can include multiple valve assemblies 800 coupled in series. In FIG. 11, a configuration including an autosampler assembly 1108, a first valve assembly (e.g., a first multiport flow assembly 1102), a second valve assembly (e.g., a second multiport flow assembly 1104), a pump assembly 1110, and a nebulizer 914 are shown. In this example, the autosampler assembly 1108 is configured to provide a sample 908 to the first multiport flow assembly 1102. The autosampler assembly 1108 can provide the means (e.g., auto-injector, robotic technology, waste, a vacuum, etc.) for providing a sample 908 into the first multiport flow assembly 1102 and/or system 1100. The first multiport flow assembly 1102 can include a valve assembly 800 as previously described (e.g., FIG. 8) and can be fluidically connected to the autosampler assembly 1108, the second multiport flow assembly 1104, and/or the pump assembly 1110. The second multiport flow assembly 1104 can include a valve assembly 800 as previously described (e.g., FIG. 8) and can be fluidically connected to the autosampler assembly 1108, the first multiport flow assembly 1102, a nebulizer 914, and/or the pump assembly 1110. The pump assembly 1110 can include a pumping system (e.g., a multiport flow assembly, a valve assembly) configured to provide multiple and/or varying liquid to the system 1100. For example, the pump assembly 1110 can include at least one pump (e.g., injector pump, peristaltic pump, etc.) that can pump at least one liquid (e.g., an eluent 904, a diluent 906, a buffer 912, deionized water, a carrier, etc.) to the first multiport flow assembly 1102 and/or the second multiport flow assembly 1104.

Figure 12:
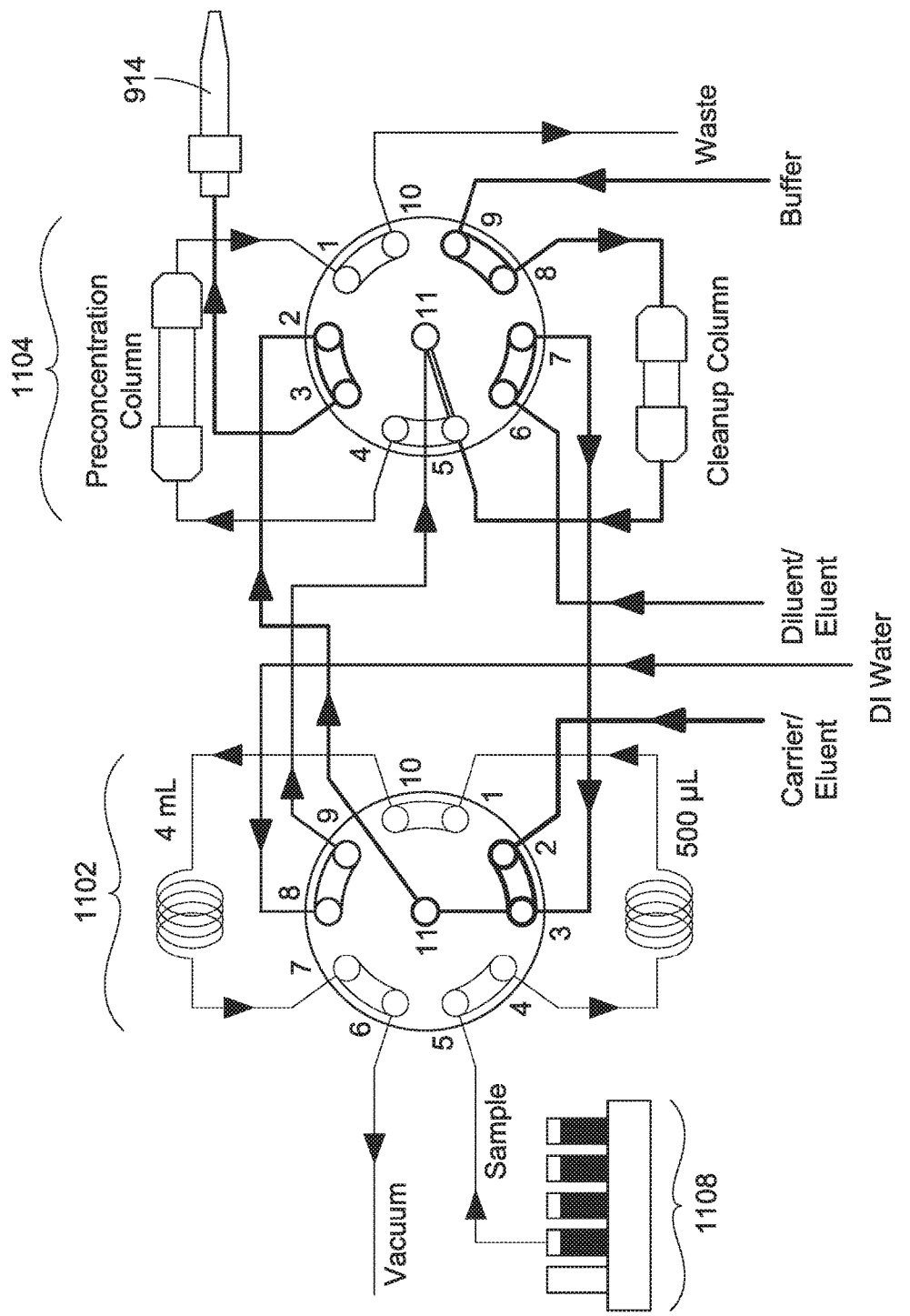
FIG. 12 is a partial diagrammatic illustration of the system shown in FIG. 11, where the first multiport flow valve assembly is arranged in a load configuration, and the second multiport flow valve assembly is also arranged in a load configuration in accordance with an example embodiment of the present disclosure.
Figure 13:
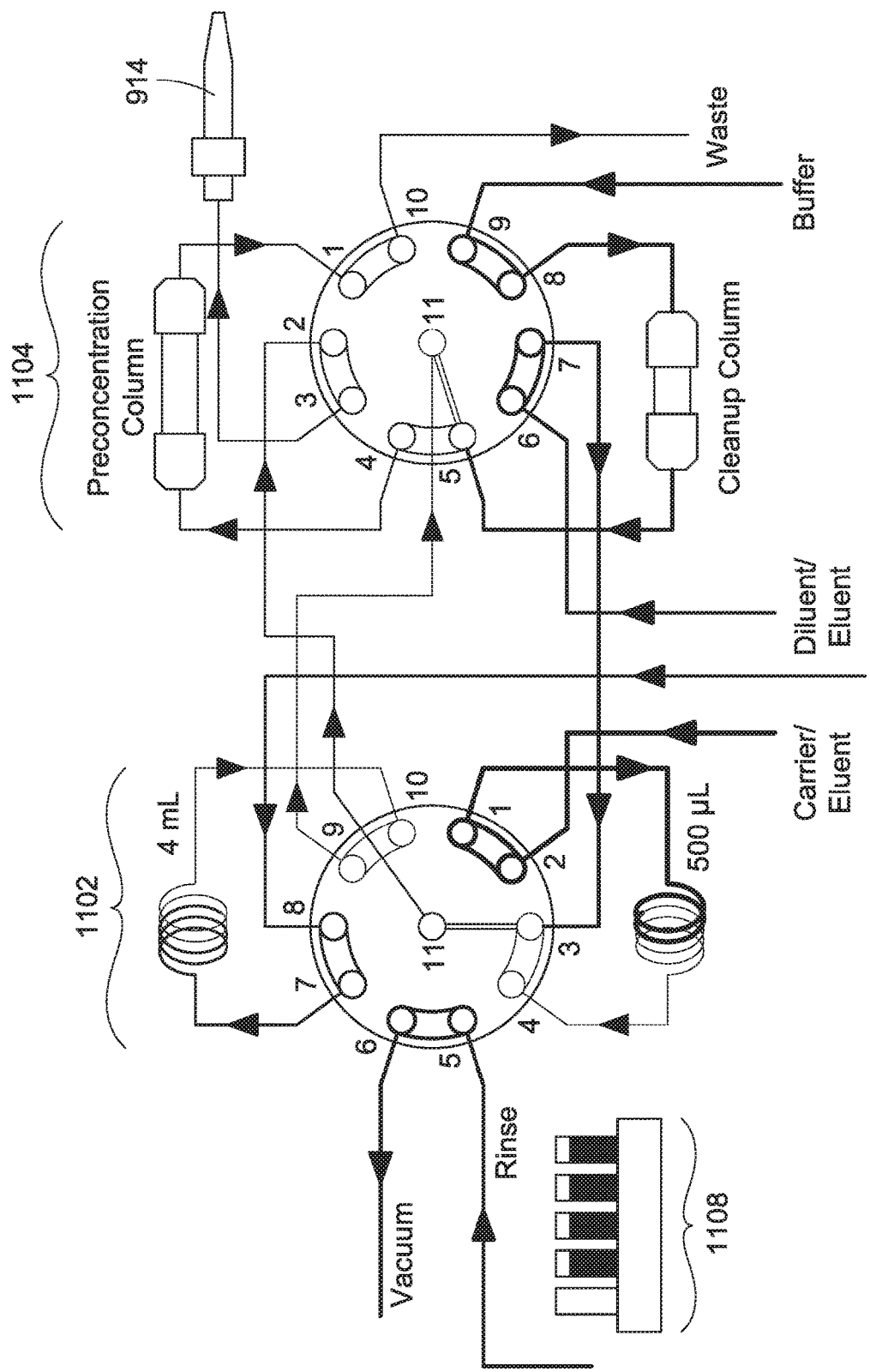
FIG. 13 is a partial diagrammatic illustration of the system shown in FIG. 11, where the first multiport flow valve assembly is arranged in a load configuration, and the second multiport flow valve assembly is arranged in an inject configuration in accordance with an example embodiment of the present disclosure.
Figure 14:
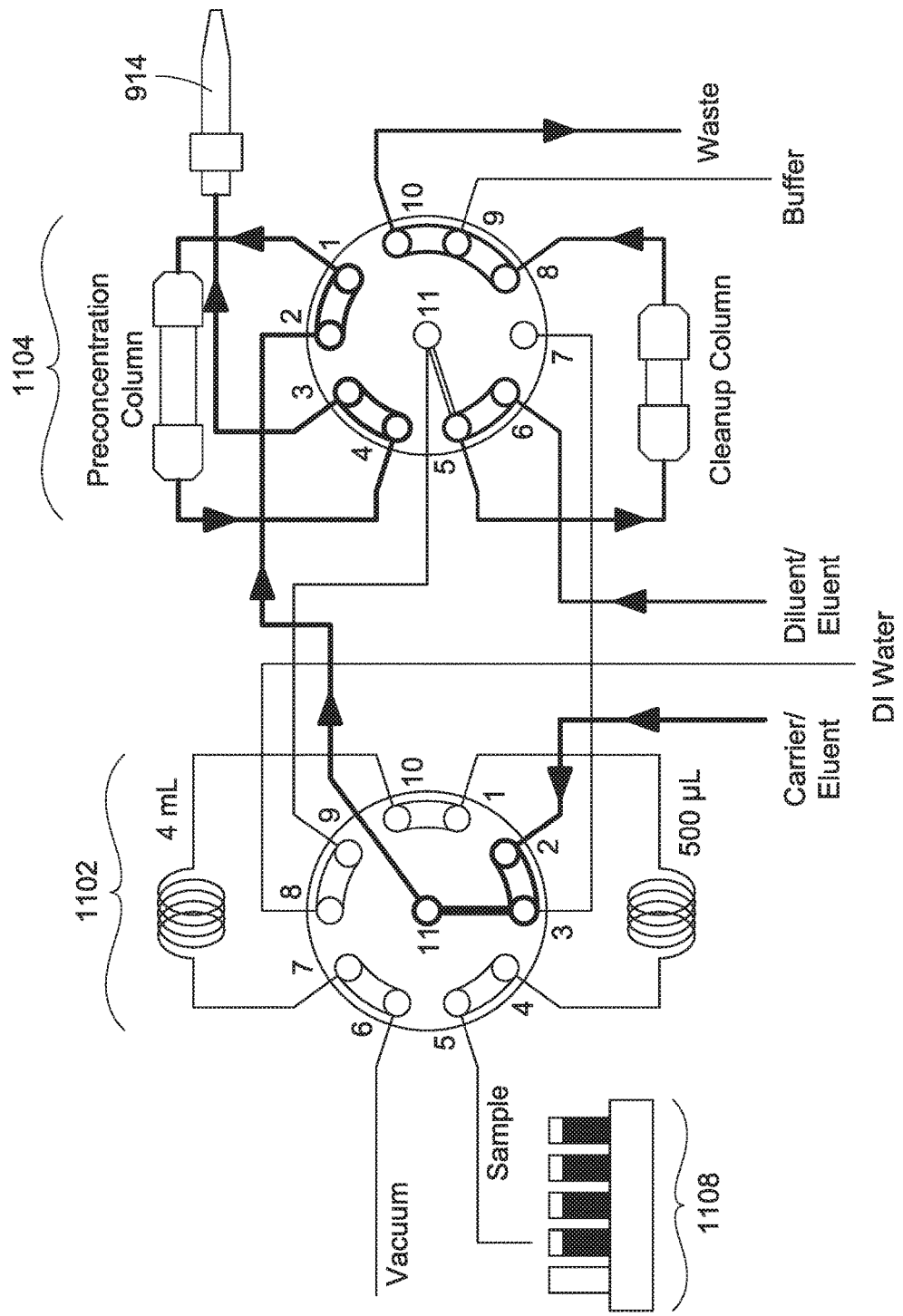
FIG. 14 is a partial diagrammatic illustration of the system shown in FIG. 11, where the first multiport flow valve assembly is arranged in an inject configuration, and the second multiport flow valve assembly is arranged in a load configuration in accordance with an example embodiment of the present disclosure.
Figure 15:
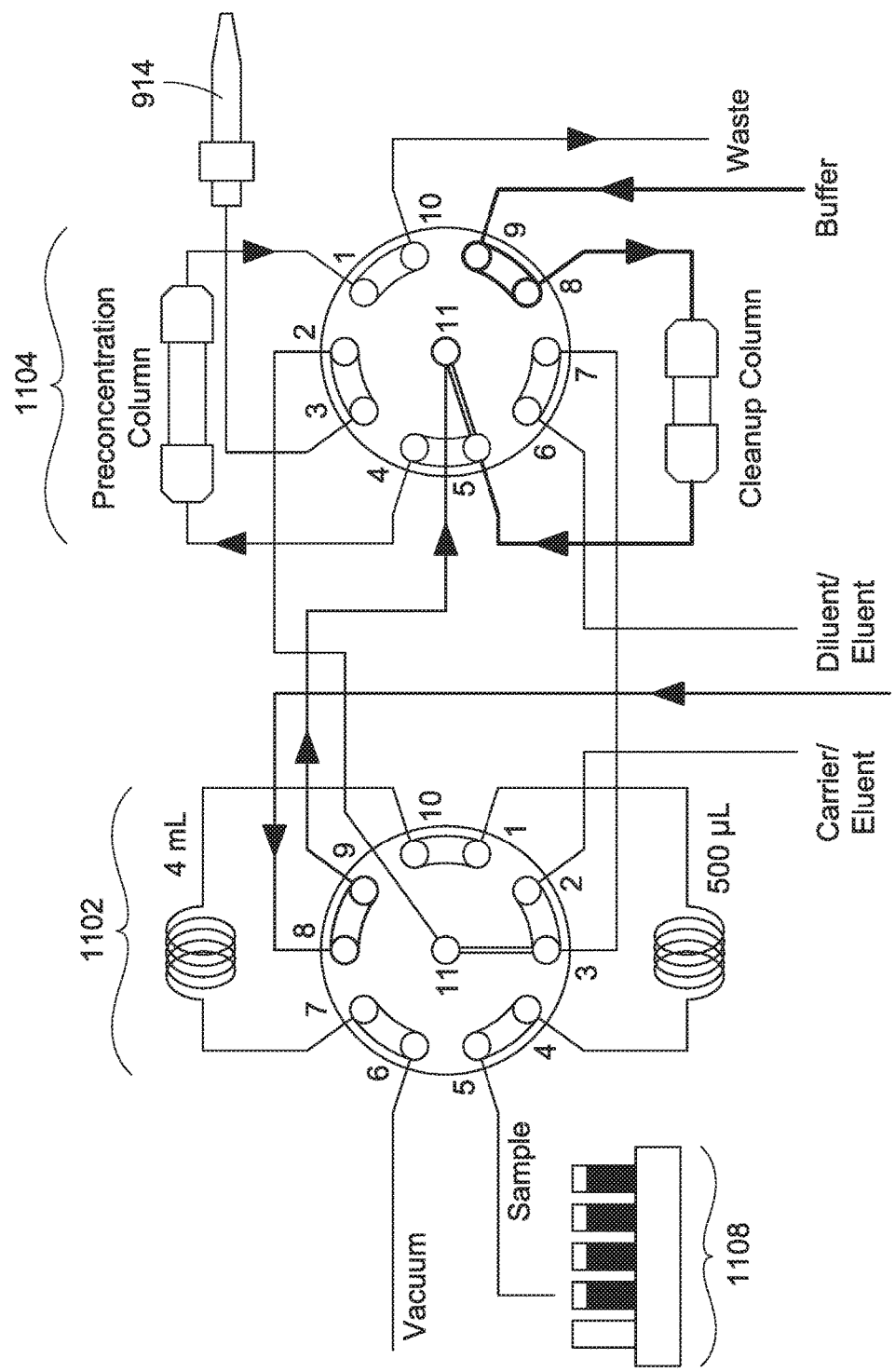
FIG. 15 is a partial diagrammatic illustration of the system shown in FIG. 11, where the first multiport flow valve assembly is arranged in a load configuration, and the second multiport flow valve assembly is also arranged in a load configuration in accordance with an example embodiment of the present disclosure.

FIG. 12 partially illustrates one configuration of a system 1100 including a first multiport flow assembly 1102 and a second multiport flow assembly 1104. In this configuration, the first multiport flow assembly 1102 is arranged in a load configuration and the second multiport flow assembly 1104 is also arranged in a load configuration. Here, the first multiport flow assembly 1102 is configured to load a sample from a sample source (e.g., autosampler assembly 1108), and the second multiport flow assembly 1104 is configured to load a diluent 906/eluent 904 and/or a buffer 912. Then, as shown in FIG. 13, a rotor 100 in the first multiport flow assembly 1102 and the second multiport flow assembly 1104 is rotated and/or adjusted such that the first multiport flow assembly 1102 is arranged in a load configuration and the second multiport flow assembly 1104 is also arranged in an inject configuration. Here, the first multiport flow assembly 1102 is configured to load a rinse solution from a sample source (e.g., autosampler assembly 1108), and the second multiport flow assembly 1104 is configured to inject the sample 908 from the first multiport flow assembly 1102 into nebulizer 914. FIG. 14 partially illustrates a subsequent rotor 100 rotation such that the first multiport flow assembly 1102 is arranged in an inject configuration and the second multiport flow assembly 1104 is arranged in a load configuration. Here, the first multiport flow assembly 1102 is configured to inject a carrier 916/eluent 904 solution into nebulizer 914 as well as load a rinse solution from a sample source (e.g., autosampler assembly 1108). FIG. 15 illustrates another rotor 100 rotation where the first multiport flow assembly 1102 is arranged in a load configuration and the second multiport flow assembly 1104 is also arranged in a load configuration, similar to the configuration in FIG. 12, where the first multiport flow assembly 1102 is configured to load a sample from a sample source (e.g., autosampler assembly 1108), and the second multiport flow assembly 1104 is configured to load a diluent 906/eluent 904 and/or a buffer 912.

Example Processes

Figure 16:
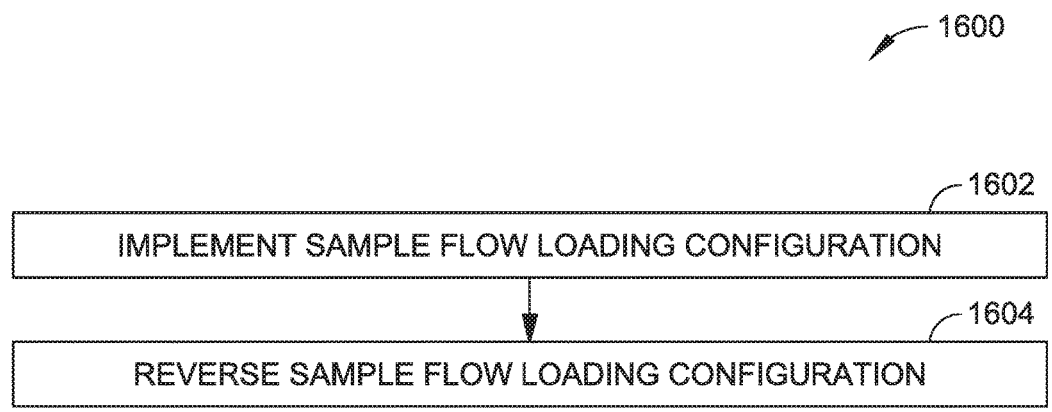
FIG. 16 is a flow diagram illustrating a process in an example implementation for using a valve assembly and system, such as the valve assembly illustrated in FIG. 8 and the system illustrated in FIG. 11.

The following discussion describes example techniques for loading and/or injecting a sample 908 into a system 1100 using a valve assembly, such as the valve assembly 800 shown in FIG. 8, a first multiport flow assembly 1102 shown in FIGS. 11-15, and/or a second multiport flow assembly 1104 shown in FIGS. 11-15. FIG. 16 illustrates process 1600 for implementing the example loading and/or injecting techniques.

As shown in FIG. 16, a sample flow loading configuration is implemented using a valve assembly (Block 1602). In embodiments, implementing a sample flow loading configuration can include using a valve assembly 800 including a first valve member (e.g, a rotor 100) and a second valve member (e.g., a stator 400), where the stator 400 includes a plurality of ports 402 including a first port 1 configured to connect to a column 902, a second port 2 configured to connect to at least one of an eluent 904 or a diluent 906, a third port 3, a fourth port 4 configured to connect to the column 902, a fifth port 5 configured to connect to a buffer 912, and a sixth port 6 configured to connect to waste 910; a second valve member (e.g., stator 400) comprising a plurality of channels 102 configured to interface with the first valve member (e.g, a rotor 100) so that the second port 2 is connected to the third port 3 and the fourth port 4 is connected to the fifth port 5 in a first configuration (e.g., a loading configuration), and the first port 1 is connected to the second port 2 and the fourth port 4 is connected to the fifth port 5 and the sixth port 6 in a second configuration (e.g., an injection configuration).

Then, the sample flow loading configuration is reversed to implement an injection configuration (Block 1602). In implementations, reversing the sample flow loading configuration to implement an injection configuration can include rotating a first valve member (e.g., rotor 100) such that a channel 104 in the rotor 100 redirects the flow through at least one port in the stator 400 resulting in a flow that is reversed along the initial flow path. In a specific example, a buffer 912 flow in a loading configuration (e.g., illustrated in FIG. 9) is pumped into port 9 and out of port 8 (port 9 and port 8 are fluidically connected using a channel 104) into a cleanup column 902. The buffer 912 flow exiting the cleanup column 902 is then pumped into port 5. In a reversing step, the rotor 100 is rotated such that a long channel 104 (e.g., at least one of the channels 104 on rotor 104 may have a first length and/or volume and at least one of the channels 104 on rotor 104 may have a second length and/or volume) is configured to fluidically connect port 8, port 9, and port 10 (e.g., shown in FIG. 10) such that the flow is reversed (e.g., flow from a diluent 906 is pumped into port 6 and out of port 5, back through the cleanup column 902 and into port 8 and out of port 10). In this embodiment, the reverse path includes from port 5, through the cleanup column, and into port 8. Rotating the rotor 100 having channels 104 with a first length and channels 104 with a second length enable the flow to be reversed.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A rotor for a valve assembly comprising:
a plurality of channels formed in a surface of the rotor, the surface configured to be adjacent to and interface with a stator having a plurality of ports, the plurality of ports including a first port configured to connect to a column, a second port configured to connect to at least one of an eluent or a diluent, a third port, a fourth port configured to connect to the column, a fifth port configured to connect to a buffer, and a sixth port configured to connect to waste, the plurality of channels fluidically connecting at least one of the first port, the second port, the third port, the fourth port, the fifth port, or the sixth port with at least one other of the first port, the second port, the third port, the fourth port, the fifth port, or the sixth port, and at least one channel that fluidically connects at least three of the plurality of ports at the rotor, wherein at least one of (A) the plurality of channels includes a channel configured to connect the second port to the third port in a first flow configuration that includes a load configuration or (B) the plurality of channels includes a channel configured to connect the fourth port to the fifth port in a second flow configuration that includes an inject configuration.

2. The rotor for a valve assembly as recited in claim 1, wherein the rotor includes a polymer material.

3. The rotor for a valve assembly as recited in claim 2 wherein the rotor includes a fluoropolymer.

4. The rotor for a valve assembly as recited in claim 1, wherein the plurality of ports includes more than six ports.

5. The rotor for a valve assembly as recited in claim 1, wherein the plurality of ports is configured to connect to an external loop, an output, and a vent.

6. A valve assembly comprising:
a first valve member; and
a second valve member comprising a plurality of ports including a first port, a second port, a third port, a fourth port, a fifth port, and a sixth port;
the first valve member comprising a plurality of channels configured to interface with the second valve member so that the second port is connected to the third port and the fourth port is connected to the fifth port in a first flow configuration, and the first port is connected to the second port and the fourth port is connected to the fifth port and the sixth port in a second flow configuration.

7. The valve assembly as recited in claim 6, wherein the third port of the second valve member includes a first channel configured to connect the second port to the third port in the first flow configuration, and the fifth port of the second valve member includes a second channel configured to connect the fourth port to the fifth port in the second flow configuration.

8. The valve assembly as recited in claim 6, wherein the first flow configuration includes a load configuration.

9. The valve assembly as recited in claim 6, wherein the second flow configuration includes an inject configuration.

10. The valve assembly as recited in claim 6, wherein the first valve member includes a rotor.

11. The valve assembly as recited in claim 6, wherein the second valve member includes a stator.

12. The valve assembly as recited in claim 6, wherein the plurality of ports is configured to connect to an external loop, an output, and a vent.

13. The valve assembly as recited in claim 6, wherein the first valve member defines a channel that fluidically connects at least three of the plurality of ports of the second valve member.

14. A process comprising:
implementing a first flow configuration using a valve assembly including
a first valve member; and
a second valve member comprising a plurality of ports including a first port, a second port, a third port, a fourth port, a fifth port, and a sixth port;
the first valve member comprising a plurality of channels configured to interface with the second valve member so that the second port is connected to the third port and the fourth port is connected to the fifth port in the first flow configuration, and the first port is connected to the second port and the fourth port is connected to the fifth port and the sixth port in a second flow configuration; and
reversing the first flow configuration to implement the second flow configuration by rotating the second valve member.

15. The process as recited in claim 14, wherein the first valve member includes a rotor.

16. The process as recited in claim 14, wherein the second valve member includes a stator.

17. The process as recited in claim 14, wherein the first valve member defines a channel that fluidically connects at least three of the plurality of ports.

* * * * *